United States Patent
Khan

(10) Patent No.: US 8,256,268 B2
(45) Date of Patent: Sep. 4, 2012

(54) SYSTEM AND METHOD FOR MEASURING POROSITY OF HIGH STRENGTH AND HIGH PERFORMANCE CONCRETE USING A VACUUM-PRESSURE SATURATION METHOD

(75) Inventor: Mohammed Iqbal Khan, Riyadh (SA)

(73) Assignee: King Saud University, Riyadh (SA)

( * ) Notice: Subject to any disclaimer, the term of this patent is extended or adjusted under 35 U.S.C. 154(b) by 492 days.

(21) Appl. No.: 12/588,959

(22) Filed: Nov. 3, 2009

(65) Prior Publication Data

US 2010/0116030 A1    May 13, 2010

Related U.S. Application Data

(60) Provisional application No. 61/193,288, filed on Nov. 13, 2008.

(51) Int. Cl.
*G01N 15/08* (2006.01)
(52) U.S. Cl. .......................................................... 73/38
(58) Field of Classification Search .................. 73/38
See application file for complete search history.

(56) References Cited

U.S. PATENT DOCUMENTS

| | | | |
|---|---|---|---|
| 2,612,036 A * | 9/1952 | Angona | 73/38 |
| 5,002,399 A * | 3/1991 | Akinc et al. | 374/14 |
| 5,373,727 A | 12/1994 | Heller et al. | |
| 6,178,808 B1 * | 1/2001 | Wang et al. | 73/38 |
| 6,321,589 B1 | 11/2001 | Regimand | |
| 6,615,643 B2 | 9/2003 | James et al. | |
| 6,684,684 B2 * | 2/2004 | Regimand et al. | 73/38 |
| 6,817,230 B2 | 11/2004 | James et al. | |
| 2005/0178189 A1 * | 8/2005 | Lenormand et al. | 73/38 |

FOREIGN PATENT DOCUMENTS

| | | |
|---|---|---|
| CN | 1073013 | 6/1993 |
| CN | 101004370 | 7/2007 |
| GB | 1197631 | 7/1970 |
| JP | 2006329961 | 12/2006 |
| NL | 8901419 | 1/1991 |
| RU | 2151394 | 6/2000 |
| RU | 2269777 | 2/2006 |

* cited by examiner

*Primary Examiner* — Hezron E Williams
*Assistant Examiner* — Nathaniel Kolb
(74) *Attorney, Agent, or Firm* — Richard C. Litman

(57) ABSTRACT

The method for measuring porosity of concrete is a vacuum pressure saturation-based method for calculating a porosity value of a sample of concrete. The method includes the steps of first drying a concrete sample and then making a first weight measurement of the concrete sample. Following the first weight measurement, the concrete sample is placed in a vacuum pressure vessel, where the sample is subjected to vacuum. The vacuum pressure vessel and a pressure cell are next filled with water. Water in the pressure cell and vacuum pressure vessel is pressurized, and the sample remains within the pressurized water for twenty-four hours. The sample remains submerged in the vacuum pressure vessel for another twenty-four hour period to achieve equilibrium. A second weight is then taken in the water, and a third weight measurement is taken in air. The porosity is calculated based upon the first, second and third weight measurements.

14 Claims, 2 Drawing Sheets

SYSTEM AND METHOD FOR MEASURING POROSITY OF HIGH STRENGTH AND HIGH PERFORMANCE CONCRETE USING A VACUUM-PRESSURE SATURATION METHOD

CROSS-REFERENCE TO RELATED APPLICATION

This application claims the benefit of U.S. Provisional Patent Application Ser. No. 61/193,288, filed Nov. 13, 2008.

BACKGROUND OF THE INVENTION

1. Field of the Invention

The present invention relates to measurement of the properties of materials, and particularly to a system and method for measuring the porosity of concrete and similar aggregate materials. More particularly, the system and method are used for measuring porosity of high strength and high performance concrete.

2. Description of the Related Art

Water absorption of aggregates is a parameter that is routinely analyzed in the design and construction of roads and structures. The ability to accurately measure water absorption of materials in a repeatable manner and in a relatively short time frame is of relative importance for engineers and practitioners interested in assessing the suitability of bulk materials and material mixtures in their projects. For example, water absorption and porosity values can yield important information about the hydraulic properties of soils and aggregates.

In the asphalt mix design industry, the absorption of aggregates in a particular design, which can include both fine and coarse aggregates, is an important assessment of the quality and suitability of the asphalt design to a particular application. The design selection of materials can be a mixture or composition of aggregates of various sizes in an assortment of different materials that can be varied to yield the desired functional characteristics or standards.

Conventional methods for measuring porosity in fine aggregates, such as concrete, typically require that a material sample of the aggregate be first oven-dried to a constant weight. The material sample is then immersed in water for a 24-hour saturation period. The sample is then spread on a flat surface and exposed to a gently moving stream of warm air until a saturated surface-dry condition is reached. To assess when the saturated surface-dry condition has been reached, the material sample is positioned into an inverted cone and lightly compacted. The cone is removed, and if the material "slumps", the material sample is considered to be in a saturated surface-dry condition. The amount of "slump" that is measured when the saturated surface-dry condition has been reached can vary from test-to-test and is operator-dependent.

Some laboratories or agencies define this condition as one in which the slump corresponds to the diameter of a dime from the top of the cone. The amount of slump can be adjusted by repetitive drying of the aggregates until the desired slump is achieved. However, if the aggregate sample is over-dried during the test procedure, the sample must be re-saturated and the drying process repeated.

After the material sample has reached the saturated dry-surface condition, a portion of the material sample is placed in a flask, which is then filled with water to a calibrated level and weighed. The fine aggregate material sample is removed from the flask and oven-dried to a constant weight. The specific gravity (apparent and bulk) and absorption are then calculated based on the three measured weights (the weight of the oven-dried sample, the weight of the flask filled with water, and the weight of the flask with the material and specimen and water to a calibration mark).

Angular fine aggregates with high absorption characteristics and/or rough surface textures do not typically slump readily. Therefore, determining the saturated surface dry (SSD) weight for samples that include these types of materials can be difficult with the cone method described above. Unfortunately, incorrect determination of this parameter in the testing process can have undesirable effects on the performance or service life of the asphalt pavement or other structure made using incorrectly analyzed materials.

In the concrete industry, the same cone test is typically used to determine the SSD condition in fine materials to determine the proper amount of water to add to the concrete mixture. Proportioning the concrete mixture with an incorrect amount of water can negatively affect the strength and durability of the concrete structures. Other commonly used methods for measuring absorption and porosity in concrete, mortar and the like include helium pycnometry, mercury intrusion porosimetry and other saturation methods, which all suffer from the repeatability problems discussed above.

For conventional concrete samples (e.g., "normal" strength concrete), conventional testing methods, such as the RILEM CPC 11.3: 1984 method (a vacuum saturation process), may be used, due to its relatively full saturation of the test samples. However, for high strength and high performance concrete samples, the RILEM CPC 11.3: 1984 method does not provide accurate measurement results because high strength and high performance concretes typically have tighter and fewer pores, with respect to conventional concrete. Thus, the RILEM CPC 11.3: 1984 method does not achieve full saturation for high strength and high performance concrete samples. Full saturation is required for accurate measurements of concrete porosity. Thus, a system and method for measuring porosity of concrete solving the aforementioned problems is desired.

SUMMARY OF THE INVENTION

The method for measuring porosity of concrete is a vacuum pressure saturation-based method for calculating a porosity value of a sample of concrete. A system for performing the method is further provided. The system includes a pressure cell, a vacuum pressure vessel, a source of pressurized air, a source of water, and a vacuum pump.

The method begins with the step of drying at least one concrete sample in an oven or the like. Then, a first weight measurement of the concrete sample is taken and recorded. Following the first weight measurement, the concrete sample is placed in the vacuum pressure vessel, where the sample is subjected to vacuum for approximately three to four hours. Application of vacuum is ceased when air is no longer being released from the pores of the sample.

The vacuum pressure vessel and the pressure cell are next filled with water from an external source of water. The pressure cell includes an interior rubber membrane, which is in fluid communication with the source of pressurized air. As the rubber membrane fills with air, water is driven out of the pressure cell and into the vacuum pressure vessel, increasing the water pressure within the vacuum pressure vessel.

The sample remains within the pressurized water for approximately twenty-four hours. After this period, the applied pressure is released from the vacuum pressure vessel and the pressure cell, restoring both the vacuum pressure vessel and the pressure cell to atmospheric pressure. The sample remains submerged in the vacuum pressure vessel for another approximately 24-hour period to achieve an equilibrium state. A second weight measurement of the sample is then taken in the water, and then a third weight measurement of the sample is taken in air. The porosity value is then calculated based upon the first, second and third weight measurements. The method is particularly useful in measuring porosity in high strength and high performance concrete samples, because high strength and high performance concretes typically have tighter and fewer pores than conventional concrete.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
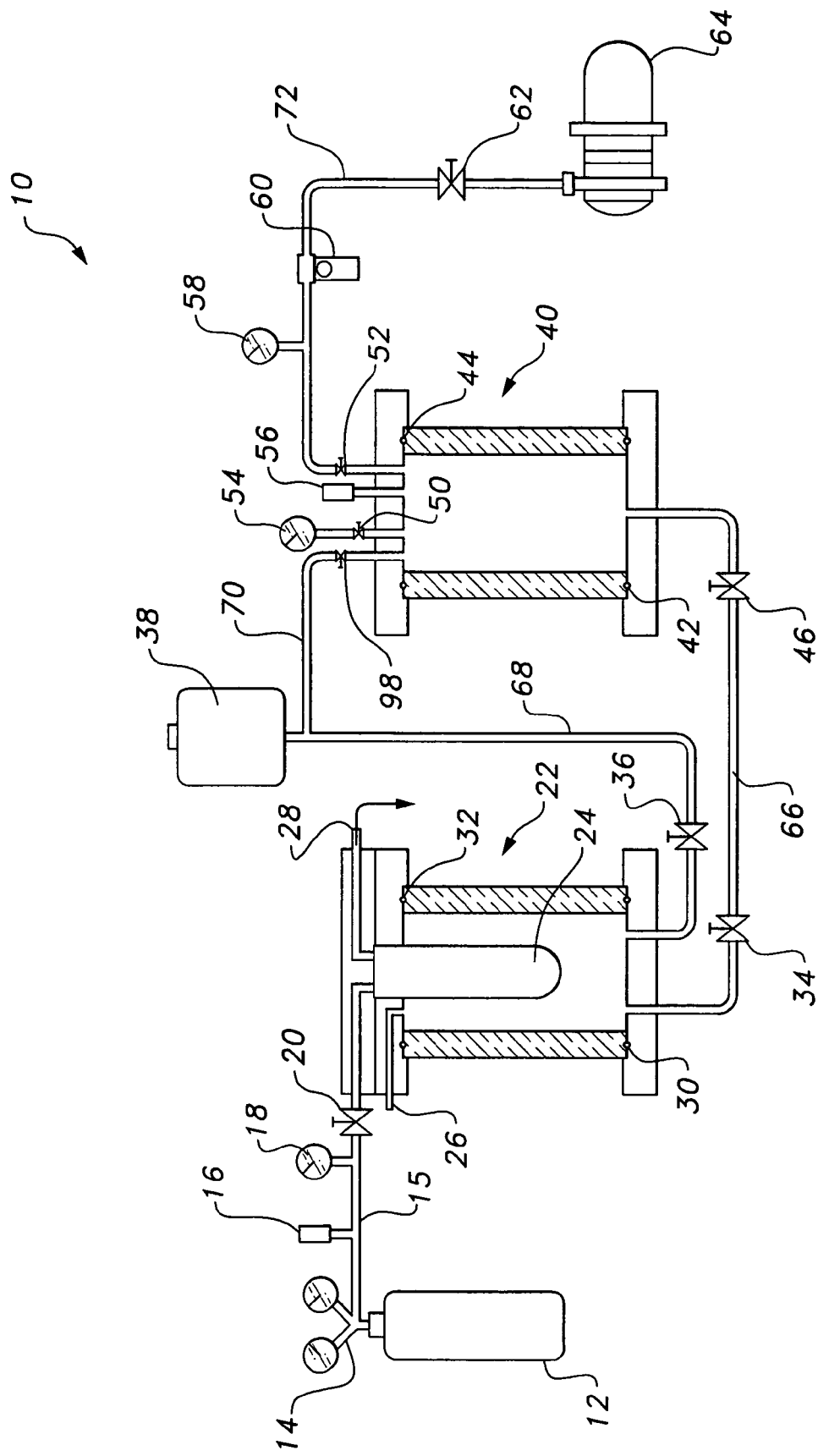
FIG. 1 is a diagrammatic view of a system for measuring porosity of concrete using a vacuum-pressure saturation method according to the present invention.
Figure 2:
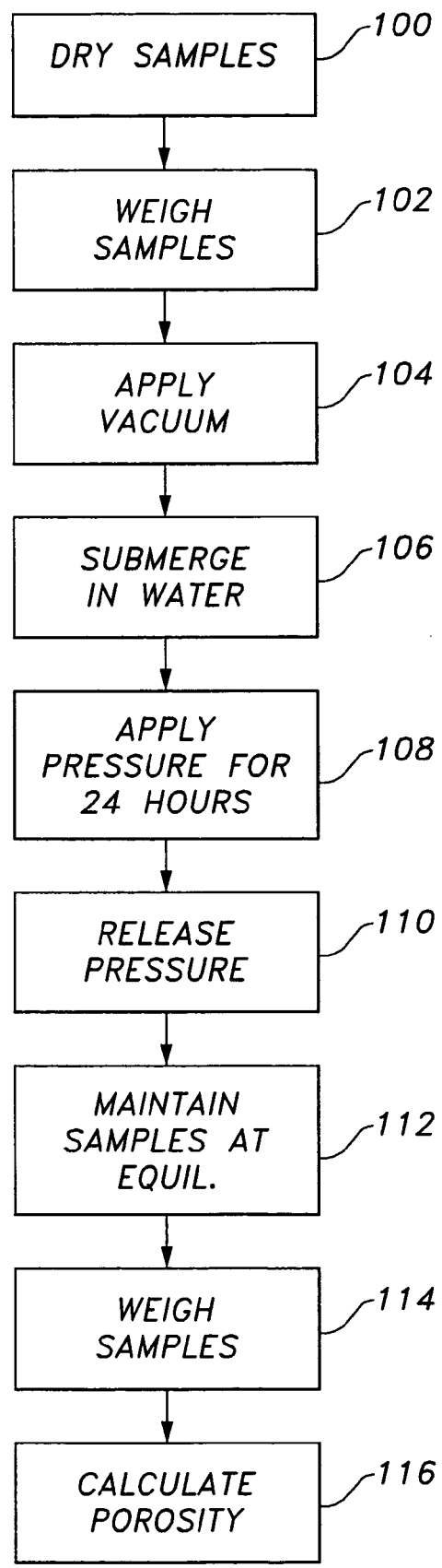
FIG. 2 is a block diagram showing the steps in a method for measuring porosity of concrete using a vacuum-pressure saturation method according to the present invention.

FIGS. 1 and 2 illustrate a system and method for measuring porosity of concrete. The method is a vacuum pressure saturation-based method for calculating a porosity value of a sample of concrete. As will be described in greater detail below, the system for performing the method primarily includes a pressure cell 22, a vacuum pressure vessel 40, a source of pressurized air 12, a source of water 38, and a vacuum pump 64.

The method begins with drying at least one concrete sample in an oven or the like (step 100 in FIG. 2) at approximately 105° C. The sample is then preferably cooled in a vacuum pressure vessel 40 for approximately twenty-four hours. Following cooling, a first weight measurement of the concrete sample is taken and recorded at step 102. Following weight measure, the sample is subjected to vacuum for approximately three to four hours (step 104) within the vacuum pressure vessel 40. As shown in FIG. 1, vacuum pressure vessel 40 is connected via vacuum line 72 to vacuum pump 64. The vacuum may be controlled via a valve 62 and a trap 60 in line 72, and may be monitored by a pressure gauge 58 or the like. Application of vacuum is ceased when air is no longer being released from the pores of the concrete sample. It should be understood that vacuum pump 64 may be any suitable type of vacuum pump, such as a rotary vacuum pump, for example. Trap 60 is provided to prevent water or moisture entering vacuum pump 64 during operation.

Application of vacuum is used to make the pores in the concrete samples fully accessible, removing any air that may be trapped therein. It should be understood that any suitable type of vacuum pressure vessel and pressure cell may be used. For example, vacuum pressure vessel 40 may be a cylindrical vessel, as shown, having an interior diameter of approximately two hundred millimeters and a height of approximately three hundred and sixty millimeters, allowing for reception of samples having volumes of up to one hundred cubic millimeters. Pressure cell 22 preferably has dimensions approximately equal to that of vacuum pressure vessel 40.

The vacuum pressure vessel 40 and the pressure cell 22 are next filled with water from the external source of water 38 (step 106). The external source of water 38 may be a water tank or the like. Both the pressure cell 22 and the vacuum pressure vessel 40 are sealed at their upper and lower ends by O-rings or gaskets 32, 30, 44, 42, respectively. Water tank 38 fills vacuum pressure vessel 40 via conduit 70 under control of valve 98, and feeds into pressure cell 22 via conduit 68 under control of valve 36. Water may feed into pressure cell 22 and vacuum pressure vessel 40 under vacuum pressure, external water pressure, or by gravity. Water tank 38 preferably holds at least approximately ten liters of water, and the water is preferably de-gasified and de-ionized.

As shown in FIG. 1, the pressure cell 22 includes an interior rubber membrane 24, forming an inflatable bladder, the interior of which is in fluid communication with the source of pressurized air 12, represented in FIG. 1 by an exemplary pressurized air tank. The water from water tank 38 fills pressure cell 22 external to membrane 24. Once the pressure cell 22 (external to membrane 24) and the vacuum pressure vessel 40 (containing the sample) have been filled with water, pressurized air is released from air supply 12. Air is fed into the interior of membrane 24 through conduit 15, regulated by an in-line regulator 14 and monitored by an air pressure gauge 18. Valve 20 allows for the control of air input into the interior of membrane 24, and a safety valve 16 may be further provided, as shown.

As the rubber membrane 24 fills with pressurized air from air source 12, water is driven out of the pressure cell 22, through conduit 66, and into the vacuum pressure vessel 40, increasing the water pressure within the vacuum pressure vessel 40 (step 108). Water flow from pressure cell 22 into vacuum pressure vessel 40 may be controlled by valves 34, 46, mounted in conduit 66. Pressure is preferably applied at between approximately twenty bars and thirty bars, measured by air pressure gauge 18 and water pressure gauge 54. Vacuum pressure saturation of the samples allows for full saturation of water within the pores of the concrete samples. The filling of rubber membrane 24 is used, as opposed to direct application of air to the water within cell 22, in order to prevent the air from dissolving in the water, which could then skew the final calculation due to air becoming trapped within the pores of the concrete samples. It should be understood that any pressurized gas may be used to fill membrane 24, such as pressurized nitrogen.

The concrete sample remains within the pressurized water in vacuum pressure vessel 40 for approximately twenty-four hours. Pressure is maintained at between approximately twenty bars and thirty bars for this twenty-four hour period. After this period, the applied pressure is released from the vacuum pressure vessel 40 and the pressure cell 22, through water vent 26 and air vent 28 (step 110). Vacuum pressure vessel 40 preferably includes a safety valve 56, allowing for release of pressure prematurely, if necessary. Pressure is released at this point to restore both the vacuum pressure vessel 40 and the pressure cell 22 to atmospheric pressure.

The sample remains submerged in the vacuum pressure vessel 40 for another approximately twenty-four hour period to achieve an equilibrium state (step 112). A second weight measurement of the concrete sample is then taken in the water, and then a third weight measurement of the concrete sample is taken in air at step 114. The porosity value is then calculated based upon the first, second and third weight measurements in step 116.

The porosity is calculated as a percentage using the formula $$P = \frac{B-A}{B-C} \times 100,$$

where P represents porosity (measured as a percentage), B represents the saturated surface dry weight (i.e., the third weight measurement, taken in air), A represents the oven dry weight (i.e., the first weight measurement), and C represents the saturated submerged weight (i.e., the second weight measurement, taken in water).

The method is particularly useful in measuring porosity in high strength and high performance concrete samples because high strength and high performance concretes typically have tighter and fewer pores than conventional concrete. Thus, as opposed to conventional techniques, such as the RILEM CPC 11.3: 1984 method, full saturation may be achieved for high performance and high strength concrete samples. Since the present method is a saturation-based method, full saturation is necessary for accurate measurement results. The method further allows for the testing of multiple samples at once.

It is to be understood that the present invention is not limited to the embodiments described above, but encompasses any and all embodiments within the scope of the following claims.

I claim:

1. A method for measuring porosity of concrete, comprising the steps of:
    drying a concrete sample;
    making a first weight measurement of the concrete sample;
    placing the concrete sample in a vacuum pressure vessel;
    subjecting the concrete sample to a vacuum;
    filling the vacuum pressure vessel with water;
    applying pressure to the vacuum pressure vessel;
    releasing the pressure applied to the vacuum pressure vessel;
    making a second weight measurement of the concrete sample while the sample is submerged in water;
    making a third weight measurement of the concrete sample in air; and
    calculating a porosity value based upon the first, second and third weight measurements.

2. The method for measuring porosity of concrete as recited in claim 1, wherein the porosity value is calculated as:

$$P=(B-A)/(B-C)\times100$$

where P represents porosity measured as a percentage, B represents the third weight, A represents the first weight, and C represents the second weight.

3. The method for measuring porosity of concrete as recited in claim 1, wherein said step of drying the concrete sample includes heating the sample.

4. The method for measuring porosity of concrete as recited in claim 3, wherein the concrete sample is heated at approximately 105° C. during the drying of the concrete sample.

5. The method for measuring porosity of concrete as recited in claim 3, wherein the concrete sample is cooled in the vacuum pressure vessel following the heating thereof and prior to said step of making the first weight measurement.

6. The method for measuring porosity of concrete as recited in claim 3, wherein said step of applying pressure to the vacuum pressure vessel includes applying water pressure at between approximately twenty bars and thirty bars.

7. The method for measuring porosity of concrete as recited in claim 6, wherein pressure is applied to the vacuum pressure vessel for a period of approximately twenty-four hours.

8. The method for measuring porosity of concrete as recited in claim 7, wherein following said step of releasing the pressure applied to the vacuum pressure vessel, and prior to the making of the second weight measurement of the concrete sample, the concrete sample remains submerged for a period of approximately twenty-four hours.

9. The method for measuring porosity of concrete as recited in claim 1, further comprising the steps of:
    filling a pressure cell with water; and
    filling an inflatable bladder submerged within the water with pressurized air, wherein the filling of the inflatable bladder drives water from the pressure cell to the vacuum pressure vessel during said step of applying pressure to the vacuum pressure vessel.

10. A method for measuring porosity of concrete, comprising the steps of:
    drying a concrete sample;
    making a first weight measurement of the concrete sample;
    placing the concrete sample in a vacuum pressure vessel;
    subjecting the concrete sample to a vacuum;
    filling the vacuum pressure vessel with water;
    filling a pressure cell with water;
    filling an inflatable bladder submerged within the water of the pressure cell with pressurized air to drive water from the pressure cell to the vacuum pressure vessel to apply pressure to the vacuum pressure vessel
    releasing the pressure applied to the vacuum pressure vessel;
    making a second weight measurement of the concrete sample while the sample is submerged in water;
    making a third weight measurement of the concrete sample in air; and
    calculating a porosity value as;

$$P=(B-A)/(B-C)\times100$$

where P represents porosity measured as a percentage, B represents the third weight, A represents the first weight, and C represents the second weight.

11. The method for measuring porosity of concrete as recited in claim 10, wherein said step of drying the concrete sample includes heating the sample.

12. The method for measuring porosity of concrete as recited in claim 11, wherein the concrete sample is cooled in the vacuum pressure vessel following the heating thereof and prior to said step of making the first weight measurement.

13. The method for measuring porosity of concrete as recited in claim 12, wherein following said step of releasing the pressure applied to the vacuum pressure vessel, and prior to the making of the second weight measurement of the concrete sample, the concrete sample remains submerged for a period of approximately twenty-four hours.

14. The method for measuring porosity of concrete as recited in claim 13, wherein the pressure is applied to the vacuum pressure vessel for a period of approximately twenty-four hours.

* * * * *